United States Patent [19]

Armour et al.

[11] Patent Number: 4,973,302
[45] Date of Patent: Nov. 27, 1990

[54] COMPACT TAMPON APPLICATOR

[75] Inventors: James C. Armour, Basking Ridge, N.J.; Kevin M. Coverdale, Hartley, Del.; Wayne D. Melvin, Camden, Del.; Michael L. Miller, Dover, Del.; Robert C. Norquest, Dover; Jamshid Rejai, Dover, Del.; Richard M. Wiernicki, Dover, Del.

[73] Assignee: Playtex Family Products Corporation, Stamford, Conn.

[21] Appl. No.: 481,668

[22] Filed: Feb. 14, 1990

Related U.S. Application Data

[63] Continuation of Ser. No. 245,888, Sep. 16, 1988, abandoned.

[51] Int. Cl.⁵ ................................................ A61F 5/44
[52] U.S. Cl. ........................................ 604/15; 604/16
[58] Field of Search ................................ 604/11–18

[56] References Cited

U.S. PATENT DOCUMENTS

| | | | |
|---|---|---|---|
| 2,222,088 | 11/1940 | Peterson | 604/17 |
| 2,355,917 | 8/1944 | Knight | 604/11 |
| 2,476,956 | 7/1949 | Bonham . | |
| 2,854,978 | 10/1958 | Millman et al. . | |
| 3,015,332 | 1/1962 | Brecht . | |
| 3,034,508 | 5/1962 | Nalle, Jr. . | |
| 3,059,641 | 10/1962 | Gershen | 604/17 |
| 3,059,642 | 10/1962 | Gershen | 604/17 |
| 3,101,713 | 8/1963 | Sargent . | |
| 3,534,737 | 10/1970 | Jones | 604/18 |
| 3,674,026 | 7/1972 | Werner et al. . | |
| 3,895,634 | 7/1975 | Berger et al. . | |
| 4,198,978 | 4/1980 | Nigro . | |
| 4,269,187 | 5/1981 | Sakurai et al. . | |
| 4,276,881 | 7/1981 | Lilaonitkul . | |
| 4,286,595 | 9/1981 | Ring . | |
| 4,291,696 | 9/1981 | Ring . | |
| 4,479,791 | 10/1984 | Sprague . | |
| 4,498,899 | 2/1985 | Gros | 604/16 |
| 4,626,238 | 12/1986 | Sustmann | 604/15 |

FOREIGN PATENT DOCUMENTS

| | | | |
|---|---|---|---|
| 1160530 | 1/1984 | Canada . | |
| 0641031 | 8/1950 | United Kingdom | 604/15 |
| 2204495 | 11/1988 | United Kingdom | 604/11 |

*Primary Examiner*—C. Fred Rosenbaum
*Assistant Examiner*—Anthony Gutowski
*Attorney, Agent, or Firm*—Stewart J. Fried

[57] ABSTRACT

A two piece compactly packaged application for a tampon which includes a discrete first member and a discrete second member, the first and the second members being of comparable length. The first and the second members are initially packaged in a side by side manner. The applicator also includes a plurality of spaced apart tabs on either the first member or the second member for retaining one of the first and the second members in the other of the first and the second members when the members are assembled together in their operative position. The method assembly of the applicator includes grasping one of the first and the second members, manually aligning the first and the second members and axially moving the first and the second members together so that the first and the second members slide relative to each other and are maintained telescopically in operative position.

14 Claims, 2 Drawing Sheets

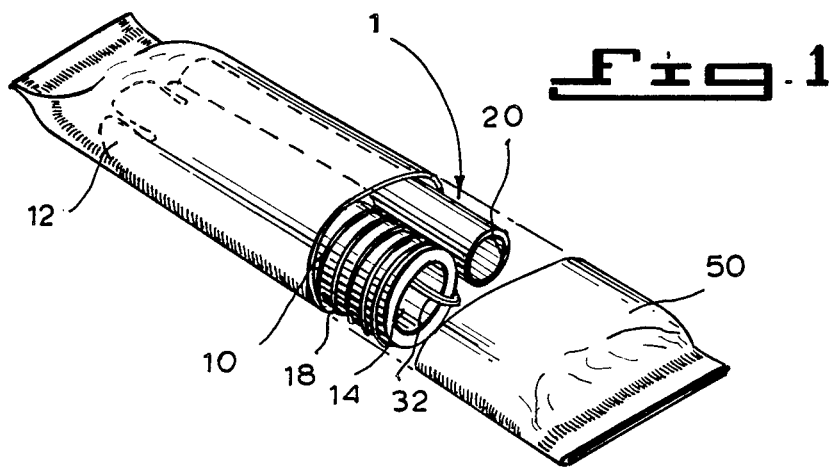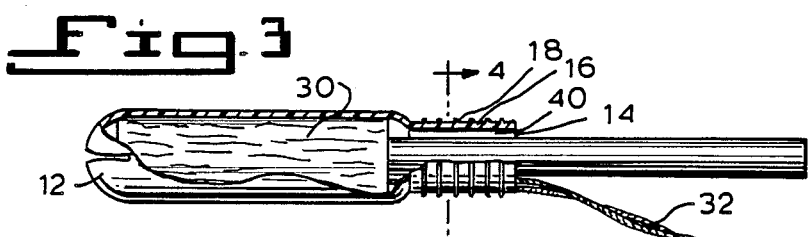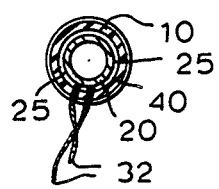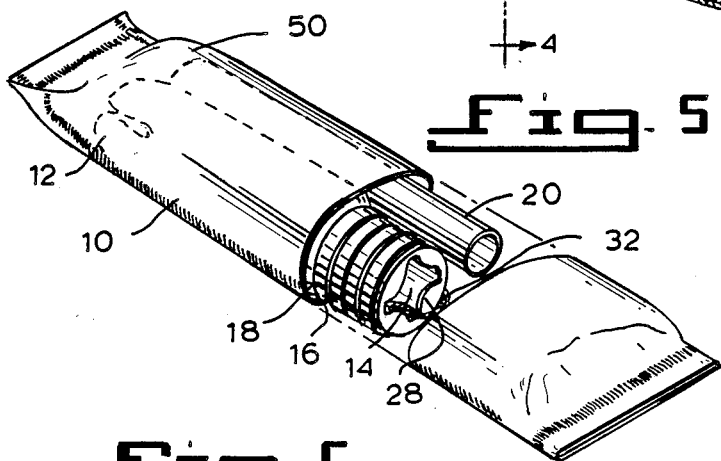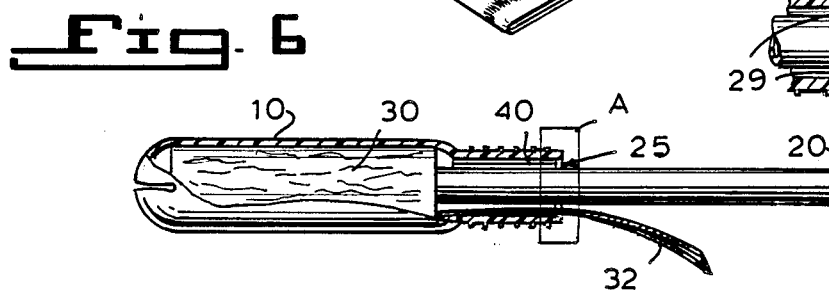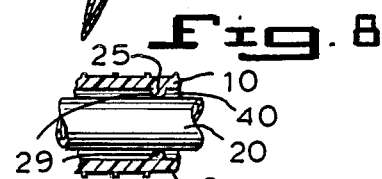

COMPACT TAMPON APPLICATOR

This application is a continuation of application Ser. No. 245,888, filed Sept. 16, 1988, now abandoned.

BACKGROUND OF THE INVENTION

1. Field of the Invention

The present invention relates generally to a tampon applicator and, more particularly, to a tampon applicator having discrete plunger and barrel components which can be compactly packaged and thereafter readily assembled together by a consumer prior to use.

The type of tampon applicator that has received widespread acceptance is one in which the applicator includes a pair of tubes having one tube, normally the plunger, adapted to move telescopically within the other tube or barrel. The tampon is normally housed at the forward end of the barrel and, to function properly, the plunger is sized to enter the rear of the barrel and extend substantially through the entire length of the barrel in order to eject the tampon Accordingly, the applicator itself is approximately two to two and one half times longer than the tampon, providing a total length in the order of 4½ to 5 inches. While this type of applicator works well, it has been found to be somewhat inconvenient for discreet handling During the menstrual period, it is recommended that women change tampons frequently. Therefore, it is necessary with today's active women that they carry replacement tampons Accordingly, there is a need for a tampon product which maintains its effectiveness, yet is small, easy to use, unobtrusive and convenient to carry on ones person, such as within a handbag. Further, there is a desire to provide such a product which does not significantly increase the manufacturing cost or the time to produce such an applicator. Many attempts have been made to reduce the overall length of the applicator, however, heretofore, all such attempted solutions have been found to be rather costly, and many are difficult to use.

2. Description of the Prior Art

Several attempts at reducing the applicator size have included having the first telescopic tube initially retracted in the second or other tube. Examples of this type of applicator are shown in U.S. Pat. No. 3,101,713 to Sargent, which issued on Aug. 27, 1963; U.S. Pat. No. 4,198,978 to Nigro, which issued on Apr. 22, 1980; U.S. Pat. No. 4,276,881 to Lilsonitkul, which issued on July 7, 1981; U.S. Pat. No. 4,286,595 to Ring, which issued on Sept. 1, 1981; and U.S. Pat. No. 4,291,696 to Ring, which issued on Sept. 19, 1981. These applicators require intricate molding techniques, and accordingly are rather costly to produce. Further, they all require several steps, such as pulling the first tube out of the second tube then locking the tubes in the extended or operational position prior to use, which steps could present some user difficulties.

Further, the retracted, telescopic applicator necessarily requires that one component, such as the plunger, be initially stored between the barrel and the tampon pledget. Accordingly, space must be provided for such storage. Therefore, at least one of the following alternatives is needed. The first alternative is that the barrel must have a cross section larger than a conventional sized barrel to provide for the plunger. The second alternative is that the tampon pledget must be made smaller in cross section to fit in the conventional sized barrel. The third alternative is that the plunger's wall thickness be made thinner than that of a conventional sized plunger. This latter alternative is dependent on the clearance that exists between the barrel and the pledget and the minimum thickness of the plunger's wall which is needed to achieve ejection of the pledget. Therefore, the third alternative most likely would need to be combined with one of the two other alternatives, provided, of course, that the plunger wall could be made thinner.

The first alternative is not desired because increasing the size of the cross section of the barrel will make the barrel wider and therefore more difficult to insert and thus probably more uncomfortable to the user during insertion. The second alternative is not desired because in order to reduce the cross section, while maintaining the same weight or amount of material, of the tampon pledget requires that the pledget be compressed further. This will make the pledget harder and therefore more uncomfortable to the user. The third alternative is not desired because reducing the wall thickness of the plunger will make the plunger less rigid and therefore may effect the ejection of the tampon pledget from the applicator. Thus, the efficiency of the applicator will be reduced.

Another approach at reducing the size of the tampon applicator has included applicators in which the plunger and barrel components are connected together in a hinge-like manner, such as the applicator shown in U.S. Pat. No. 4,269,187 to Sakurai, et al, which patent issued on May 26, 1981. However, these type applicators, due to insufficient rigidity, may require an undesired increase in user force needed to eject the tampon.

Further attempts to reduce the applicator's size include providing the plunger and the barrel detached and requiring assembly of the components prior to use. These type applicators readily lend themselves to a commercial product and resolve the length concern associated with the conventional, unitary tampon applicator. However, these applicators raise other concerns. A principal concern is the ability of the barrel and plunger to remain in place after assembly. A second concern is the ability to provide for the non-interfering placement of the tampon string within the assembled applicator. A third concern is maintaining the relatively low tampon ejection force associated with a unitary tampon applicator. A fourth concern is the ability to take out the plunger while advantageously holding the barrel in the wrap so as to avoid having the user touch the barrel of the applicator.

Attempts to overcome the problems have required that the barrel or the plunger or both, be radically altered or a new component added, to positively retain the plunger in the barrel. These changes have significantly increased the manufacturing and production costs of the commercial product. Moreover, these types of applicators may have increased the friction force required to slide the plunger in the barrel and thus have increased the force needed to eject the tampon.

For example, U.S. Pat. No. 3,674,026 to Werner et al., which issued on July 4, 1972, is directed to a tampon insertion device which requires a new component, a cap, to enable the inserter rod or plunger to be connected to the barrel and to provide for the positioning of the string Specifically, the insertion device includes a barrel having a tapered, segmented tip end, a fitted disc-shaped cap which is adapted to close the opposite end of barrel, and a detachable inserter rod. Also, the cap is provided with a first, centrally disposed aperture for receiving the inserter rod and a second, marginally disposed aperture through which the tampon string is placed.

It should be noted that in some conventional length applicators, the end of the plunger located in the barrel is flanged to retain the plunger in the barrel. See, for example, U.S. Pat. No. 2,476,956 to Bonham, which issued on July 26, 1949; U.S. Pat. No. 2,854,978 to Millman, et al, which issued on Oct. 7, 1958; U.S. Pat. No. 3,895,634 to Berger, et al, which issued on July 22, 1975; and the commercial tampon products sold by Playtex Family products, Inc. under the registered trademark PLAYTEX (of Playtex Apparel, Inc.). Also in U.S. Pat. No. 4,479,791 to Sprague, which issued on Oct. 30, 1984, projections were provided on the inner wall of the barrel and adapted to mate in a groove provided in the exterior wall of the plunger to hold the plunger in the barrel. In these conventional length applicators, the plunger is factory assembled in the barrel by the manufacturer. Therefore, there is not present the possibility that during assembly by the consumer there will be damage or inadvertent ejection of the tampon therein.

Conventional length tampon applicators have attempted to minimize the drag force caused by the plunger sliding in the barrel or vice versa by providing locators to position effectively and guide the plunger during sliding in the barrel. For example, U.S. Pat. No. 3,015,332 to Brecht, which issued on Jan. 2, 1962, is directed to a conventional length, tampon applicator having a plunger which telescopically slides in the barrel of the applicator. Specifically, the barrel has a plurality of axially extending ribs on its inner surface. The ribs extend axially basically throughout the barrel and extend radially inward towards the center axis of the barrel a short distance to form bearing surfaces upon which the plunger rests. This patent does not consider the problem of having a consumer position the string during assembly. Also, since the bearing surfaces are relatively long, they could increase the undesired friction force between sliding components and thus the force to eject the tampon. Further Brecht requires a close frictional fit between the plunger and barrel to prevent his plunger from rocking or tilting. Due to Brechts' (1) very rigid engagement between the plunger and barrel, (2) relatively long ribs and (3) flat surfaces along the tops of the ribs, if the string were placed between Brecht's plunger and barrel (as contrasted to his disclosed location of the string within the plunger), there is a substantial probability that the string will get caught between the plunger and barrel, making the applicator inoperative.

Canadian Patent No. 1,160,530 to Voss, which issued on Jan. 17, 1984, and which is directed to a conventional sized application, provides a plurality of inwardly projecting dimples or lobes arranged in equally spaced circumferential relation around the inner wall of the applicator tube or barrel to guide the plunger and the hygienic medium for longitudinal advancement in the applicator tube. Each of the plurality of dimples is of a generally convex or spherical configuration.

Thus, there has not, heretofore, been provided a relatively simple and inexpensive two piece applicator which lends itself to a compact package, provides means integral to either the plunger or the barrel to retain the plunger and barrel in their assembled state and, moreover, provides for placement of the string. Further, there has not been such an applicator which also minimizes the sliding or the drag force which normally occurs by the plunger sliding within the barrel.

SUMMARY OF THE INVENTION

Against the foregoing background, it is a primary object of the present invention to provide a two piece compactly packaged applicator for ejecting a tampon.

It is another object of the present invention to provide such an applicator in which the barrel and the plunger are packaged side-by-side thereby reducing the length of the packaged tampon.

It is yet another object of the present invention to provide such an applicator which provides a significant savings in cost of materials combined with ease of assembly by the consumer and in which the non-interference placement of the tampon string in the assembled applicator is automatically accomplished.

It is still yet another object of the present invention to provide such an applicator in which the end of the barrel is not touched during assembly.

To the accomplishments of the foregoing objects and advantages, the present invention, in brief summary, comprises a two piece applicator for a tampon. The two piece applicator includes a discrete first member and a discrete second member. The first and the second members are of comparable length. There is also provided means, formed on either the first member or the second member, for retaining one of the first and the second members in the other of the first and the second members. The applicator, when initially packaged, has the first and the second members in a side by side manner in the package or wrap.

The present invention also includes the method of assembly of such a two piece tampon applicator. Specifically, the first and the second members are aligned and then one of the first and the second members is slid into the other of the first and the second members.

BRIEF DESCRIPTION OF THE DRAWINGS

The foregoing and still other objects and advantages of the present invention will be more apparent from the following detailed explanation of the preferred embodiments of the invention in connection with the accompanying drawings wherein:

FIG. 1 is a perspective view of one embodiment of the applicator of the present invention as positioned in a commercial package;

FIG. 2 is a side view of the plunger of the embodiment of FIG. 1;

FIG. 3 is a sectional side view of the assembled applicator of FIG. 1;

FIG. 4 is a sectional view taken along lines 4—4 of FIG. 3;

FIG. 5 is a perspective view of another embodiment of the applicator of the present invention;

FIG. 6 is a sectional side view of the assembled applicator of FIG. 5;

FIG. 7 is an end view of the assembled applicator of FIG. 5;

FIG. 8 is an enlarged section view of region A of FIG. 6; and

DESCRIPTION OF THE PREFERRED EMBODIMENTS

Figure 9:
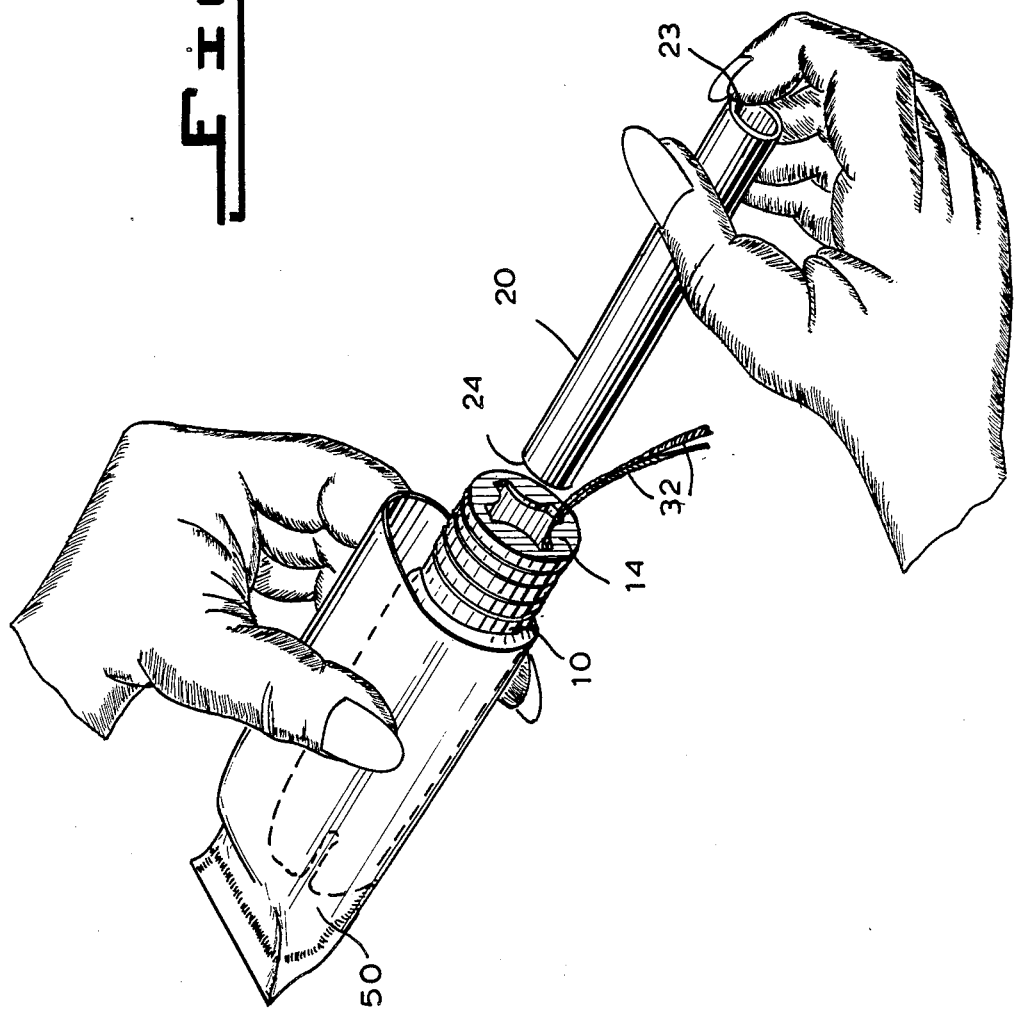
FIG. 9 is a perspective view of the tampon applicator of FIG. 5 being assembled by a consumer.

Referring to the figures and, in particular, FIG. 1, there is provided a tampon applicator generally represented by reference numeral 1. The tampon applicator includes a discrete barrel 10 and a discrete plunger 20. The barrel 10 and the plunger 20 are basically of the same or comparable length. In a commercial product, the barrel 10 and the plunger 20 are packed in their disassembled state, such as in a side by side manner in a wrap 50 as shown in FIG. 1. The ultimate customer, the consumer, will then assemble the applicator 1 together prior to use as shown in FIG. 3. The wrap 50 shown in FIG. 1 is the subject of a co-pending application Ser. No. 245,832 (now U.S. Pat. No. 4,881,644), which was filed on even date.

Referring to FIGS. 1-3, the barrel 10 provides a hollow tube for housing therein a conventionally sized tampon 30 having a tampon string 32. The barrel 10, preferably, has a petal-tip end 12 through which the tampon 30 is ejected from the barrel, and an opposite or plunger receiving end 14 for receiving the plunger 20. The plunger receiving end 14 of the barrel 10, preferably, has a necked down portion 16. Specifically, the necked down portion 16, preferably, has both the inside and outside diameters less than the respective diameters of the remainder of the barrel 10. However, the plunger receiving end 14 of the barrel 10 could have its inside diameter or its outside diameter or both the same as the remainder of the barrel. The exterior of the necked down portion 16 of the barrel 10, also preferably, has a fingergrip area 18 which may have a series of circumferential ribs, score lines, embossments or the like, which serve as fingergrips to enable the tampon user to readily grasp the applicator. It should be understood that the features of the tampon and the applicator, such as petal tips necking down of one end of the barrel and use of fingergrips have been known in the art, for example as shown in U.S. Pat. No. 3,895,634 to Berger, et al., which issued on July 22, 1975.

The barrel 10 and plunger 20 components of the applicator 1 can be made of any suitable plastic material. A preferred plastic material is polyethylene. It is most preferred that the barrel 10 be made of low density polyethylene and the plunger 20 be made of high density polyethylene thereby making the barrel more flexible than the plunger. Alternatively, the barrel 10 and plunger 20 can be made of cardboard.

As shown in FIG. 2, the plunger 20 is basically a cylindrical, hollow tube and, except for protrusions or tabs 25, has uniform inside and outside cross-sections along its axial extent. On the outside surface of the plunger 20, there is, preferably provided to opposed protrusions 25 which serve to position and to secure or retain the plunger in place in the barrel 10. The precise placement of the protrusions 25 on the plunger 20 may vary slightly, but the preferred placement is as close to the barrel end 24 of the plunger that the equipment for forming the protrusions on the plunger shall permit. The reason for this placement is to avoid disturbing the tampon 30 in the barrel 10 during assembly by the consumer but prior to use, and to minimize the length of the plunger. It has been found that the center of each protrusion 25 should be approximately three-sixteenths to three-eights of an inch from the edge of the end 24.

In the embodiment shown in FIG. 2, the protrusions 25, as stated above, preferably, comprise a pair of opposed protrusions which are formed by knurling, punching or staking a portion of the outside surface of the plunger 20. By using these knurling, punching or staking techniques, it is relatively easy and inexpensive to form the protrusions 25 on the plunger 20. It should be understood that one, or three or more protrusions can be used, however a pair of protrusions 25 are preferred since they serve to secure the plunger 20 in position in the barrel 10 yet minimize the number of surface contact points between the plunger and barrel. The minimization of the number of surface contact points is desired since the greater the number of points, the greater the friction force that must be overcome to slide the plunger 20 in the barrel 10 and eject the tampon 30 from the barrel. The use of a pair of opposed protrusions 25 also positions the plunger 20 in direct axial alignment with the barrel 10 so that the radial extent of space 40 is uniform. Accordingly, plunger 20 is less likely to strike the inside surface of the barrel 10 during operation, which striking would also increase the force needed to eject the tampon 30 from the barrel. Further, the use of a pair of protrusions 25 provides more space thereby facilitating the placement of the tampon string 32 in the space 40 during assembly of the applicator 1.

Referring to FIG. 4, the actual dimensions of the outside diameter of the plunger 20 and the inside diameter of the barrel 10 may vary. However, the relationship of these diameters should be such that the outside diameter of the plunger 20 is slightly less than the inside diameter of the barrel 10, or tampon containing component, to create the space 40 therebetween. The space 40 serves to readily permit the plunger 20 to slide in the barrel 10 without contacting or striking the inside surface of the barrel. It is, preferred, that the outside diameter of the plunger 20 be approximately 0.283 inches ±0.015 inches, and that the inside diameter of the barrel be approximately 0.355 inches ±0.015 inches. Each of the protrusions 25 extends radially outward from the plunger's outer surface an amount equal to or slightly greater than the space 40 so that the tip of each protrusion just touches the inside surface of barrel 10. In one preferred embodiment, the protrusions extend radially outward approximately 0.040 inches ±0.015 inches thereby just contacting the inside surface of the barrel 10. Accordingly, the plunger 20 shall remain in position and shall not fall out, yet there is provided only minimal resistance to the plunger sliding in the barrel. The space 40 also serves to permit placement of the tampon string 32 between the plunger 20 and barrel 10. Due to the protrusions 25, it has been found that when one attempts to insert the plunger in operative position, i.e. in the barrel 10, the tampon string 32 automatically or naturally falls in space 40 in the area between the protrusions 25

FIG. 5 illustrates a second preferred embodiment which is analogous to the FIG. 1 embodiment in that the barrel 10 and plunger 20 are provided in a side-by-side fashion in a tampon wrap 50. The barrel 10 has the tampon ejection end 12, which preferably is petal-tipped, and the plunger receiving end 14, preferably with the necked down portion 16, as shown in FIG. 6. Also, the exterior of the plunger receiving end 14 includes a fingergrip area 18 which may be located on the necked down portion 16.

As shown in FIG. 6, the plunger 20 of this embodiment has a uniform cylindrical cross-section throughout its axial extent. Also, plunger 20 has an outer diameter sized slightly smaller than the inside diameter of the barrel 10 so as to form circumferential space 40 between the plunger and the barrel.

As shown in FIGS. 6 and 7, the barrel 10 has on its inside surface the protrusions or tabs 25. The tabs 25 are located in the plunger receiving end 14 of the barrel 10 and as close to the edge of the plunger receiving end as permitted by the barrel forming equipment. It has been found that the tabs 25 can be placed at the actual edge of the plunger receiving end 14 of the barrel 10. The tabs 25 extend from the inside surface of barrel 10 radially inward towards the center axis of the barrel 10. While two or more tabs could be used, four tabs are preferred to assure optimal alignment and securement of the plunger 20 in the barrel 10. It is also preferred that the tabs be equally spaced apart. Between each adjacent pair of tabs 25 there is formed a clearance 28 which serves as a tampon string receiving area in the space 40 formed by the inside surface of the barrel 10 and the outside surface of the plunger 20.

As with the protrusions or tabs 25 in the FIG. 1 embodiment, the protrusions or tabs 25 of the FIG. 5 embodiment extend radially inward an amount equal to or slightly greater than the radial extent of space 40. Accordingly, the tip 29 of each tab 25 contacts the outer surface of plunger 20 to hold the plunger in place in the barrel 10. In this embodiment, it is preferred that each tab 25 extends radially inward a distance of about 0.045 to about 0.048 inches. It has been found that with the plunger 20 having an outside diameter of approximately 0.283 inches ±0.015 inches and the inside diameter of the barrel 10 having a diameter of approximately 0.355 inches ±0.015 inches, the tabs 25 press only slightly against the outer surface of the plunger. Accordingly, the friction force between the barrel 10 and the plunger 20 during operation is minimized.

Each tab 25 is relatively very thin in axial extent and, as shown in FIG. 8, has an arcuate, radiused tip 29. These features also serve to minimize the friction force created when the plunger slides in the barrel during the ejection of the tampon and during assembly of the applicator since the tabs have the ability to flex, i.e act like a hinge. It is preferred that the axial extent of the tip 29 be between about 0.008 to about 0.011 inches.

Referring again to FIG. 1, when the top of the tampon wrap 50 is removed, the plunger receiving end 14 of barrel 10 and the other end 23, opposite the barrel end 24 (see FIG. 2), of the plunger 20 are exposed.

To assemble the tampon applicator of the FIG. 1 and the FIG. 5 embodiments from the disassembled state illustrated in FIGS. 1 and 5, respectively, to the operative state or position illustrated in FIGS. 3 and 6, respectively, the user, as shown in FIG. 9, preferably, grasps the main portion or barrel containing portion of the wrap 50 between the thumb and the index finger of one hand and grasps, with the other hand, the opposite end of the wrap (the end nearest end 23 of the plunger 20 and end 14 of the barrel 10) to snap the wrap apart to expose the disassembled tampon. The plunger 20 is then removed from the wrap 50 and end 24, the nongrasped end, is aligned with the plunger receiving end 14 of the barrel 10. The plunger 20 and the barrel 10 are then axially moved together by moving one or both components. Thus, the preferred method of assembly allows the user to assemble the tampon applicator without touching with their fingers the functional or tampon ejection end 12 of the barrel 10.

During such assembly, the string of the tampon will automatically fall in the clearance space between the tabs, as shown in FIGS. 4 and 7. The clearance space, when the applicator is in its assembled state, is a portion of space 40. Thereafter, the assembled plunger and barrel is removed from the wrap 50.

In the FIG. 1 embodiment, the user grasps the plunger 20 at end 23 to insert the opposite or protrusion end 24 into the plunger receiving end 14 of the barrel. This orientation is necessary in this embodiment to assure that the protrusion end 24 is positioned in the plunger receiving end 14 of the barrel 10. Protrusions 25 on end 24 will frictionally engage the inner surface of plunger receiving end 14 of the barrel 10 to position and secure the plunger in place in the barrel.

In the FIG. 5 embodiment, the tabs are located on the inside of the barrel 10. Significantly, the user can grasp either end 23 or end 24 of the plunger 20. Thus the orientation of the plunger needed in the FIG. 1 embodiment is not needed in this FIG. 5 embodiment. Also in this embodiment, the tabs 25 bend towards the petal-tip end 12 of the barrel 10 when the plunger 20 contacts the tabs to securely position the plunger in the barrel.

Having thus described the invention with particular reference to the preferred forms thereof, it will be obvious that various changes and modifications may be made therein without departing from the spirit and scope of the invention as defined by the appended claims.

Wherefore, we claim:

1. A two piece applicator for a tampon which includes a string, comprising:
   a discrete first hollow cylindrical member;
   a discrete second hollow cylindrical member, said first and second members being of comparable length;
   said tampon located in one of said members with the string extending outward of said member;
   said members being movable between a first condition wherein said first member and said second member are initially packaged adjacent each other in a side by side manner along their entire length with their longitudinal axes being in spaced apart substantially parallel relationship, and a second condition wherein the cylindrical members are assembled together with one of said members inserted within the other in coaxial relationship;
   means located on either said first member or said second member, for retaining one of said first and second members in telescoping relationship with the other of said first and second members when said first and second members are in said second condition;
   said retaining means including a clearance means between the adjacent cylindrical surfaces of said first and second members in their second condition; and
   wherein said tampon string automatically positions in said clearance means when said cylindrical members are moved from said first condition to said second condition, whereby said string extends between and outward of the assembled cylindrical members.

2. The applicator of claim 1, wherein said retaining means is formed on the exterior cylindrical surface of one of said first and second members.

3. The applicator of claim 1, wherein said retaining means is formed on the interior cylindrical surface of one of said first and second members.

4. The applicator of claim 1, wherein said retaining means includes a plurality of radially projecting and arcuately spaced apart tabs which extend between the cylindrical interior surface of one of said members and the exterior cylindrical surface of the other of said members; and said clearance means formed of a plurality of openings between the adjacent radial surfaces of said spaced apart tabs, whereby said string automatically falls into one of said openings when said applicator members are moved to said second condition 5. A tampon assembly comprising:

A tampon having a string;

said tampon enclosed within a discrete barrel member; and a discrete plunger member, said plunger and said barrel members having comparable lengths; and means formed on either the inner surface of said barrel member or outer surface of said plunger member, for retaining said plunger in said barrel in telescoping relationship when said barrel and said plunger are assembled together, said retaining means including a plurality of axially thin, radially projecting and arcuately spaced apart tabs between the outer surface of said plunger and inner surface of said barrel, said tabs being axially limited to the extreme end region of one of said barrel or said plunger members and adapted to provide an axial flexure of said tabs during engagement between said barrel and plunger members, each adjacent pair of said plurality of tabs defining a clearance opening therebetween of minimal axial extent which is adapted to receive the said tampon string positioned in one of said clearance openings in non-interfering relationship between the relatively movable outer surface of said plunger and inner surface of said barrel.

6. The applicator of claim 5, wherein said barrel inner surface and plunger outer surface are cylindrical and said retaining means is formed on said inner cylindrical surface of said barrel.

7. The applicator of claim 6, wherein said outer plunger surface and inner barrel surface are separated by an annular gap, and said retaining means includes a plurality of equally spaced apart thin, axially flexible tabs about the entire circular extent of said 8. The applicator of claim 7, wherein each of said plurality of tabs has a tip, each tip being approximately 0.008 to 0.011 inches in axial extent.

9. The applicator of claim 5, wherein said plunger outer exterior surface and barrel inner surface are cylindrical and said retaining means is formed on said outer cylindrical surface of said plunger.

10. The applicator of claim 6 wherein each of said tabs has an axial extent in the order of 0.008 to 0.011 inches.

11. The applicator of claim 6 wherein each of said tabs extends from the outer most end of the barrel an axial amount in the order of 0.008 to 0.011 inches.

12. The applicator of claim 6 wherein each of said tabs has an arcuate, radiused tip.

13. The applicator of claim 10 wherein in each of said tabs has an arcuate radiused tip.

14. A method for assembly of two piece tampon applicator, said tampon applicator including:

a cylindrical barrel member containing a tampon with a string;

a cylindrical plunger member of substantially the same length as said barrel member; and a plurality of arcuately spaced apart tabs formed on either said plunger or said barrel members, which extend between the outer cylindrical surface of the plunger and inner cylindrical surface of the barrel, for retaining said plunger member in said barrel member in telescoping relationship when said plunger and said barrel members are assembled together in operative position;

said method comprising the steps of:

grasping at least one of said plunger and said barrel members;

manually aligning said plunger member with said barrel member; and automatically positioning the tampon string in one of the openings between adjacent spaced apart tabs, in non interfering relationship between the outer cylindrical surface of the plunger and inner cylindrical surface of the barrel while simultaneously axially moving said plunger and barrel members together so that said plunger and said barrel members slide relative to each other and are maintained telescopically in operative position.

* * * * *

UNITED STATES PATENT AND TRADEMARK OFFICE
CERTIFICATE OF CORRECTION

PATENT NO. : 4,973,302
DATED : November 27, 1990
INVENTOR(S) : James C. Armour, et. al.

It is certified that error appears in the above-indentified patent and that said Letters Patent is hereby corrected as shown below:

Column 9, line 47, after "said" insert --annular gap--.

Signed and Sealed this

Twenty-second Day of February, 1994

Attest:

BRUCE LEHMAN

Attesting Officer           Commissioner of Patents and Trademarks